United States Patent [19]

Krafft

[11] Patent Number: 5,380,895
[45] Date of Patent: Jan. 10, 1995

[54] METHOD FOR THE SYNTHESIS OF METAL ALKYLS AND METAL ARYLS

[75] Inventor: Terry Krafft, Longmont, Colo.

[73] Assignee: Bandgap Technology Corporation, Broomfield, Colo.

[21] Appl. No.: 16,585

[22] Filed: Feb. 10, 1993

[51] Int. Cl.$^6$ ............................ C07F 3/08; C07F 3/10; C07F 5/00; C07F 7/08

[52] U.S. Cl. ........................................ 556/1; 556/121; 556/187; 556/478; 556/7; 556/95; 556/98; 556/129

[58] Field of Search ................... 556/1, 121, 187, 478, 556/7, 95, 98, 129

[56] References Cited

U.S. PATENT DOCUMENTS

| | | | |
|---|---|---|---|
| Re. 33,292 | 8/1990 | Bradley et al. | 556/1 |
| 4,599,150 | 7/1986 | Mullin et al. | 204/59 QM |
| 4,720,560 | 1/1988 | Hui et al. | 556/1 |
| 4,847,399 | 7/1989 | Hallock et al. | 556/1 |

OTHER PUBLICATIONS

Eisch et al., *Organometallic Synthesis,* vol. 2, Academic Press, pp. 89–90 (1981).
Bradley et al., 1988, "Lability of dimethylethyl compounds of indium and aluminium," Chemtronics 3:159–161.
Clark et al., 1967, "Organoindium Chemistry: I. A. Convenient Preparation of Dimethylindium(III) Derivatives," Journal of Organometallic Chemistry 8:427–434.
Coates et al., 1956, "Co-ordination Complexes of Methyl Derivatives of Indium and Thallium," J. Chem. Soc. pp. 3351–3354.
Dennis et al., 1934, "Indium Trimethyl," J. American Chemical Society pp. 1047–1049.
Eisch, 1962, "Organometallic Compounds of Group III. I. The Preparation of Gallium and Indium Alkyls from Organoaluminum Compounds", J. American Chemical Society 84(19):3605–3610.
Foster et al., 1988, "Synthesis and Thermal Properties of Adducts of Trimethylindium with Nitrogen–containing Lewis Bases," J. Chem. Soc. Dalton Trans. (1988) p. 7.
Jones et al., 1986, "Analysis of High Purity Metalorganics by ICP Emission Spectrometry," Journals of Crystal Growth 77:47–54.
Krommes et al., 1973, "Eine Verbesserte Darstellungsmethode Fur Indiumtrimethyl," Inorg. Nucl. Chem. Letters 9:587–589.
Moore et al., 1986, "High Mobility InP Epitaxial Layers Prepared by Atmospheric Pressuer Movpe Using Trimethylindium Dissociated from an Adduct with 1,2–Bis(Diphenyl Phosphino)Ethane," Journal of Crystal Growth 77:19–22.
Runge et al., 1951, "Indiumorganische Verbindungen,"0 Zeitschrift fur anorganische und allgemeine Chemie, Band 267, pp. 39–48.
Stone, 1958, "Stability Relationships Among Analogous Molecular Addition Compounds of Group III Elements," Chemical Reviews 58:117–129.
Todt et al., 1963 "Darstellung von Indium–trialkylen uber In–Mg–Legierung oder–Mischung," Zeitschrift fur anorganische und allgemeine Chemie, Band 321, pp. 120–123.
Zanella et al., 1991, "Organometallic Precursors in the Growth of Epitaxial Thin Films of Groups III–V Semiconductors by Metal–Organic Chemical Vapor Deposition," Chem. Mater. 3(2):225–242.

*Primary Examiner*—José G. Dees
*Assistant Examiner*—Porfirio Nazario-Gonzalez
*Attorney, Agent, or Firm*—Pennie & Edmonds

[57] ABSTRACT

Method for forming metal alkyl compounds by the direct combination of metal halide, lithium metal, and alkyl or aryl halide and for purifying metal alkyl compounds by repeated sublimation/pumping cycles. The method can be used to produce metal alkyl compounds which are substantially free of volatile impurities.

12 Claims, No Drawings

METHOD FOR THE SYNTHESIS OF METAL ALKYLS AND METAL ARYLS

BACKGROUND OF INVENTION

1. Technical Field

The subject invention relates to the synthesis volatile organometallic compounds having the formula $$MR_n$$

where M is a metal from groups IIB, IIIB or IVB of the Periodic Table, each R is independently selected from alkyl and aryl and combinations thereof; and n is an integer determined by the valence of M.

2. Background Art

Compounds between elements of group III-A and of group V-A of the Periodic Table are of economic value as semiconductor materials in electronic and optoelectronic applications. To be suitable for use in electronic devices, the III-V materials must be prepared under very stringent conditions of chemical purity. The current state of the art is such that the requisite conditions to deposit thin films of III-V compounds can be attained only by a few sophisticated deposition methods, such as OMVPE (organometallic vapor phase epitaxy) or MOCVD (metal organic chemical vapor deposition) and MBE (molecular beam epitaxy). P. Zanella, et al., Chemistry of Materials 3, 225–242, 225 (1991).

In such approaches, a common method of introducing the Group II, III, IV and V compounds is as a volatile metal alkyl compound (e.g., trimethylindium). P. Zanella, et al., at page 226. It is generally accepted that the purity level of these precursor alkyls currently limits the obtainable purity of the resultant epitaxial layer of III–V compound, which in turn determines the technological usefulness of the resultant device. P. Zanella, et al., at page 226. Accordingly, techniques which limit the levels of impurities in the metal alkyl compounds are of great value in improving the quality of the III-V semiconductor.

Because the metal alkyl compounds are typically transferred in the vapor phase, the most detrimental impurities are those which are volatile. Both the method of synthesis and the method of purification determine what volatile impurities will be present.

Consider the illustrative case of indium, a group IIIB metal. There are several known methods of synthesis of trialkyl indium compounds:

1. $In + 1.5\ HgR_2 \rightarrow R_3In + 1.5\ Hg$ L. M. Dennis, et al., J. Am. Chem. Soc. 56, 1047 (1934); P. Krommes, et al., J. Inorg. Nucl. Chem. Letters 9, 587 (1973). This method can leave behind volatile and toxic mercury and mercury compounds.

2. $InCl_3 + 3 RLi \rightarrow R_3In + 3\ LiCl$ H. C. Clark, et al., J. Organometal. Chem. 8, 427 (1967). The alkyllithium reagent reacts with trace oxygen and water, and must be standardized immediately before use. After exposure to air or water, the alkyllithium reagent can be contaminated with $R_2$ and R-OH species, which must be removed from the $R_3In$ product.

3. $InCl_3 + 3\ RMgCl \rightarrow R_3In + 3\ MgCl_2$ V. F. Runge, et al., Z. Anorg. Allg. Chem. 267, 39 (1951); D. F. Foster, et al., J. Chem. Soc., Dalton Trans., 7 (1988). The Grignard reagent RMgCl is pyrophoric.

4. $In + 3.5\ Mg + 5\ RBr \rightarrow R_3In + 1.5\ MgBr_2 + 2RMgBr$ V. E. Todt, et al., Z. Anorg. Allg. Chem. 321, 120 (1963). The reactions are slow and reactive by-products are formed.

5. $In + RMgCl + ether + electrolysis \rightarrow R_3In$ J. B. Mullin, et al., U.S. Pat. No. 4,599,150 (1986). The reagent RMgCl can react with air and water. There is a low yield of $R_3In$ product.

6. $InCl_3 + 3\ R_3Al + 3\ KCl \rightarrow R_3IN + KAlR_2Cl$ J. J. Eisch, J. Am. Chem. Soc. 84, 3605 (1962); A. C. Jones, et al., J. Cryst. Growth 77, 47 (1986); A. H. Moore, et al., J. Cryst. Growth 77, 19 (1986); R. B. Hallock, et al., U. S. Pat. No. 4,847,399 (1989). The reagent $R_3Al$ can react with air and water. There is a low yield of product.

Methods 1–3 and 5–6 all use reactive, liquid-phase reagents which react with air and water to create secondary impurities which must be removed from the $R_3In$ product. The liquid-phase reagents must be standardized before use. Method 4 creates a reactive, liquid-phase product which reacts with air and water. Thus, all previous methods involve working with a reactive, liquid-phase reagent which creates difficulties during synthesis and additional complexity in the purification step.

How effectively the metal alkyl compound can be purified determines the impurity level and value of the final semiconductor product. To remove volatile impurities from volatile metal alkyl compounds such as trialkyl indium, the art teaches a purification process comprising:

a) reaction of the volatile trialkyl metal compound to form a product of lower volatility. The art teaches complex formation of the trialkyl metal compound with a Group VB-containing Lewis base. D.C. Bradely, et al., U.S. Pat. No. Re 33,292 (1990); and D. F. Foster, et al., J. Chem. Soc., Dalton Trans., 7 (1988). The art also teaches adduct formation in the presence of excess $R_xM$, where R=alkyl group, M=a group I-A or II-A metal. R. B. Hallock, et al., U.S. Pat. No. 4,847,399 (1989);

b) pumping off the volatile impurities. Of course, any impurities which became involatile because of the chemistry of complex or adduct formation will not be removed; and c) regeneration of the volatile trialkyl metal.

The art thus teaches a three step approach to purification involving conversion of the trialkyl indium to nonvolatile species, pumping of impurities, and regeneration of volatile species.

SUMMARY OF THE INVENTION

It is the most important object of the present invention to simplify the synthesis of alkyl or aryl metal compounds by generating the product in one step with reagents which are of high purity, which do not tend to form volatile impurities during shelf life, and which do not require frequent standardizations.

An aspect of the invention is the direct reaction of metal halide, $MX_n$. (M=metal of group IIB, IIIB or IVB; X=Cl, Br or I; n=an integer to satisfy the valence), with the alkali metal lithium, in the presence of alkyl or aryl halides RX' (R=an alkyl group containing from about 1 to about 10 carbon atoms or an aryl group containing from about 6 to about 20 carbon atoms or mixtures thereof; X'=Cl, Br or I) to form $R_nM$ and lithium halide according to the following reaction:

$$MX_n + 2nLi + nRX' \rightarrow R_nM + nLiX + n\ LiX'$$

Unlike the reactive, liquid-phase reagents previously taught by the art, elemental lithium metal used in the present invention can be obtained in high purity, does not form volatile impurities during shelf life, and does not require frequent standardizations to determine concentration.

Another important object of the present invention is to simplify the purification of metal alkyl compounds by allowing the removal of volatile impurities without converting the metal alkyl compound to a less volatile chemical form.

An aspect of the invention is the discovery that the product metal alkyl can be purified without conversion to a less volatile form. Repeated cycles of sublimation and pumping have been found sufficient to remove volatile impurities to satisfactory limits.

The purification technique could be applied to other volatile species not covered by the synthesis portion of this patent. Any sublimable compound could be purified of volatile impurities by this method.

DESCRIPTION OF THE PREFERRED EMBODIMENT

The first step is the formation of metal alkyl from the combination of metal polyhalide, lithium metal, and alkyl or aryl halide. The preferred indium trihalide is indium trichloride. The preferred alkyl halide is alkyl bromide. The combination is done under inert gas.

The solvent is a hydrocarbon or an ether substantially stable to alkali metal, preferably diethyl ether.

The preferred sequence of addition is to add metal polyhalide to the lithium, followed by addition of the ether. The alkyl or aryl halide is added to this mixture at a rate sufficient to maintain reflux of the solution. Optionally, the mixture may be heated at reflux both during and after the addition of the alkyl or aryl halide.

Having formed the product metal alkyl, the next step is to separate the polyalkyl metal from the nonvolatile coproducts either by distillation, decantation or filtration.

Once the crude product metal alkyl is separated, the next step is to remove the solvent by distillation and then to purify the product by sublimation or distillation to remove the volatile impurities.

As an example of a purification method, we have discovered that slow sublimations under static vacuum in a closed system can be highly effective for removing ether from trimethyl indium. The method is simple and has advantages over other purification methods including conventional sublimation. In a conventional sublimation the product is normally condensed onto a cold finger under dynamic vacuum. Use of dynamic vacuum results in loss of product and poor control of the crystallization rate leads to incorporation of impurities. The new method employs static vacuum which eliminates loss of product and allows for the slow recrystallization of the trimethyl indium which excludes impurities.

The purification method of the present invention can be generally applied to removing volatile impurities from sublimable compounds. This method comprises:
a) placing a sublimable compound containing volatile impurities in a closed system at a temperature at which the sublimable compound is a solid;
b) establishing a vacuum in the system by pumping away any gases which may be present, either by employing conventional freeze-pump-thaw methods or by pumping until the pressure drops to a nearly steady state;
c) isolating the system after establishing a vacuum as described above;
d) maintaining one portion of the system which is away from the sublimable compound at a lower temperature than that of the sublimable compound to cause the compound to crystallize at such portion of the system at a rate which excludes impurities from the crystallizing compound;
e) removing any volatile impurities liberated during the recrystallization by evacuating the system until the pressure reaches a nearly steady state; and
f) repeating steps a) to e) until a desired purity is achieved.

By this purification method, sublimable compounds other than trimethyl indium could be purified, including compounds such as trimethylamine alane, $AlH_3 \cdot NMe_3$, and copper hexafluoroacetylacetonate, $Cu(hfac)_2$.

The following examples are given by way of illustration and not by way of limitation.

EXAMPLE 1

Part 1. Preparation of trimethyl indium.

Battery grade lithium (30.63 g, 4.41 mol; 99.96%) was cut up under argon and added to a 2 liter three-necked flask fitted with a mechanical stir shaft and a stopcock. $InCl_3$ (154.98 g, 0.7006 mol; 99.999%) was added and the flask was then fitted with a reflux condenser and maintained under a nitrogen atmosphere. After the condenser was cooled to $-5°$ C., diethyl ether (1700 milliliter; 99.9%; dried and distilled from $LiAlH_4$) was added through a Teflon ® cannula. With constant stirring, an excess of methyl bromide (260 g, 2.74 mol; 99.5%) was added through a subsurface gas delivery tube over a period of 7 hours. The reaction initiated immediately and methyl bromide was added at a sufficient rate to maintain reflux.

After the addition was complete, the mixture was heated at reflux for 2 hours and allowed to stand for 1 hour. The liquids were siphoned away from the lithium chloride and lithium bromide by-products and passed through a Schlenk filter into a 2 liter flask which was fitted with a Claissen tube, still head, condenser and receiver. The solids were washed twice with 400 milliliters of ether and the washings siphoned and filtered into the distillation flask. Ether was distilled until the liquid volume was about 350 milliliter.

The distillation apparatus was replaced by a u-tube attached to a 1 liter, 3-neck flask connected to a vacuum manifold. The receiver was cooled with liquid nitrogen and the ether/trimethyl indium mixture was vacuum transferred away from the remaining lithium salts. Near the end of the transfer the lithium salts were heated to 100° C. to ensure complete removal of the product. Nuclear magnetic resonance analysis of the trimethyl indium/ether solution indicated a 96.5% yield of crude product.

Part 2. Purification of trimethyl indium.

The solution was transferred to a sublimator and sublimed over 5 hours with the cold finger at $-10°$ C. Nuclear magnetic resonance analysis indicated that the product contained 0.4 weight% ether (99.19 g of trimethylindium, 88.2% yield).

The product was further purified by conducting sublimations under static vacuum in a closed vessel and by pumping out the head space for 20 seconds between each sublimation. The ether concentration dropped from its initial value of 9,000 ppm (molar basis) to about 17 ppm after 10 cycles. After the eleventh cycle, no ether could be detected by nuclear magnetic resonance.

EXAMPLE 2

Preparation of triethyl indium

The same general method described in Example 1 was employed for synthesis of triethyl indium. Lithium (5.92 g, 0,853 mol; 99.96%), indium trichloride (29.95 g, 0.1354 mol; 99.999%) and diethyl ether (350 milliliters; 99.9%; distilled from LiAlH$_4$) were combined in a 500 milliliter flask. With constant stirring, ethyl bromide (56 g, 0.514 mol; 99% from Aldrich) was added over a period of 2 hours.

After refluxing for 2 hours, the liquids were siphoned through a Schlenk filter into 1 liter flask. The solids were washed twice with 150 milliliter of ether and the washings siphoned and filtered into the distillation flask. Ether was distilled until the liquid volume was about 50 milliliters. The ether/triethyl indium mixture was then vacuum transferred away from the remaining salts and nuclear magnetic resonance analysis indicated a 99.2% yield of crude product. The product was purified by vacuum distillation. Nuclear magnetic resonance analysis indicated that the product contained 4.3 weight % ether (25.46 g of triethylindium, 93% yield).

EXAMPLE 3

Preparation of dimethyl cadmium

The method described in Example 1 was employed for the synthesis of dimethyl cadium. Lithium foil (3.498 g, 0.504 mol; 99.96%) was cut up and combined with CdCl$_2$ (21.998 g, 0.120 mol; 99%) and diethylether (250 milliliter, 99.9%; distilled from LiAlH$_4$) in a 500 milliliter flask. MeBr (29.5 g, 0.311 mol; 99.5%) was added over a period of 2 hours. After refluxing for 2 hours, an additional aliquot of MeBr (5.0 g, 0.053 mol) was added and the mixture was heated under reflux overnight.

The solution was cooled and after the solids settled for 1 hour, the liquids were siphoned through a Schlenk filter into a 1 liter flask. The solids were washed twice with ether and the washings siphoned into the distillation flask. Ether was distilled until the head temperature rose to ~33° C. The ether/Me$_2$Cd mixture was vacuum transferred away from the remaining salts to a receiver cooled with liquid nitrogen. NMR analysis indicated a 56% yield of crude product.

EXAMPLE 4

Preparation of tetramethyl tin

The method described in Example 1 was modified for synthesis of tetramethyl tin. Lithium foil (4.70 g, 0.677 mol; 99.96%) was cut up and combined with diethylether (250 milliliter; 99.9%; distilled from LiAlH$_4$) in a 500 milliliter three-necked flask. SnCl$_4$ (20.32 g, 0.078 mol; 99%) was slowly added to the reaction through an addition funnel. With constant stirring, methyl bromide (MeBr) (42 g, 0.442 mol; 99%) was added over a period of 2.5 hours and the mixture was heated under reflux overnight. An additional aliquot of MeBr (6.0 g, 0.063 mol) was added and the reaction heated for 2 hours.

The mixture was allowed to cool and settle for 1 hour. The liquids were filtered into a 1 liter flask and the solids were washed twice with ether. The solution was concentrated to 100 milliliters by distilling ether through a vigreux column. The ether/Me$_4$Sn mixture was vacuum transferred away from the residual salts and NMR analysis indicated a 51% yield of crude product.

EXAMPLE 5

Removal of volatile impurities from trimethyl indium

Trimethyl indium was vacuum transferred to a glass storage vessel and weighed (37.74 g). Aliquots of dimethyl zinc (0.20 g), dimethyl cadmium (0.18 g), tetramethyl silane (0.17 g), tetramethyl tin (0.21 g), and tetramethyl germanium (0.19 g) were condensed into the vessel. The mixture was heated above the melting point of trimethyl indium to ensure homogeneity. The volatile impurities were removed by repeated cycles of sublimation under static vacuum followed by pumping of the head space. The sublimations were conducted by maintaining the impure trimethyl indium at room temperature (20°-25° C.) at one end of the cylindrical vessel and maintaining a temperature of 10°-15° C. at the other end of the vessel. During each sublimation the trimethyl indium recrystallized in the cold zone within about 24 hours. After each sublimation was complete, the system was opened to a vacuum source for 15-20 seconds to remove volatile impurities liberated during the recrystallization. The sublimation was then repeated by cooling the opposite end of the vessel.

Initially the vapor pressure of the contaminated sample was measured at 108 torr. Before the first sublimation was begun, the head space was pumped for 20 seconds to reduce the high vapor pressure resulting from the impurities. This was necessary because the rate of sublimation drops off significantly with increasing pressure. For the same reason, the head space was also evacuated four times during the course of the first sublimation.

After ten sublimation/pumping cycles, 95% of the product was recovered. A sample of the purified material was hydrolyzed and analyzed by spark source mass spectrography and by inductively coupled plasma mass spectroscopy. The analyses indicated that zinc, cadmium, germanium and tin levels in the purified trimethyl indium were less than 1 ppm by weight. The silicon concentration was determined by inductively coupled plasma optical emission spectroscopy and was less than the instrument detection limit of 1.7 ppm by weight.

It is apparent that many modifications and variations of this invention may be made without departing from the spirit and scope thereof. The specific embodiments described are given by way of example only and the invention is limited only by the terms of the appended claims.

A number of references are cited in the present specification, the entire disclosure of each of which is incorporated by reference herein, in its entirety.

What is claimed is:

1. A method of synthesizing metal alkyl compounds of the formula MR$_n$ comprising
  a) mixing lithium metal and a metal halide of the formula MX$_n$, wherein M is a metal selected from the Groups consisting of IIB, IIIB or IVB of the Periodic Table; X is a halide selected from the group consisting of chlorine, bromine and iodine; and n satisfies the valence of the metal M; and
  b) combining an alkyl or aryl halide of the formula RX' with the lithium metal/metal halide mixture of a) to form the metal alkyl or aryl compound R$_n$M and solid lithium halide in the final reaction mixture, wherein R is independently selected from the group consisting of alkyl groups containing from about 1 to about 10 carbons atoms and of aryl groups containing from about 6 to about 20 carbon atoms and X' is selected from chlorine, bromine and iodine.

2. The method according to claim 1 wherein the metal halide is added to the lithium prior to adding the alkyl or aryl halide.

3. The method according to claim 1 wherein the metal halide is added to the lithium simultaneously with the addition of alkyl or aryl halide.

4. The method according to claim 1 wherein the reaction is performed in a solvent which does not substantially react with the lithium metal, the metal halide, or the alkyl or aryl halide.

5. The method according to claim 1 wherein the reaction is performed in the absence of a solvent.

6. The method according to claim 1 further comprising the steps of
  c) removing the solid lithium halide from the final reaction mixture by decantation, filtration, or distillation of the product;
  d) separating the metal alkyl or aryl compound from the mixture by distillation; and
  e) purifying the separated metal alkyl or aryl compound by distillation or sublimation.

7. The method according to claim 6 in which the metal alkyl or aryl compound after step e) is further purified of volatile impurities by
  f) placing the metal alkyl or aryl compound in a closed system at a temperature at which the compound is a solid;
  g) establishing a vacuum in the system by pumping away any gases which may be present, either by employing conventional freeze-pump-thaw methods or by pumping until the pressure drops to a nearly steady state;
  h) isolating the system after establishing a vacuum;
  i) maintaining a portion of the system which is away from the compound at a lower temperature than that of the compound to cause the compound to crystallize at such portion of the system at a rate which excludes impurities from the crystallizing compound;
  j) removing any volatile impurities liberated during the recrystallization by evacuating the system until the pressure reaches a nearly steady state;
  k) repeating steps f) to j) until a desired purity is achieved.

8. The method according to claim 1 wherein the alkyl halide is selected from methyl chloride, methyl bromide, methyl iodide, ethyl chloride, ethyl bromide ethyl iodide or mixtures thereof.

9. The method according to claim 1 wherein the metal halide is indium trichloride to thereby produce a trialkylindium or triarylindium compound and solid lithium halide.

10. The method according to claim 4 wherein the solvent is diethylether, pentane, hexane, heptane or mixtures thereof.

11. The method according to claim 9 wherein the alkyl halide is methyl halide to thereby produce trimethylindium.

12. The method according to claim 9 wherein the alkyl halide is ethyl halide to thereby produce triethylindium.

* * * * *